United States Patent
Ries et al.

(10) Patent No.: US 11,331,108 B2
(45) Date of Patent: May 17, 2022

(54) MEDICAL DEVICE

(71) Applicant: JOIMAX GMBH, Karlsruhe (DE)

(72) Inventors: Wolfgang Ries, Linkenheim (DE); Lars Schendzielorz, Linkenheim (DE); Rainer Steegmüller, Gerlingen (DE)

(73) Assignee: JOIMAX GMBH, Karlsruhe (DE)

( * ) Notice: Subject to any disclaimer, the term of this patent is extended or adjusted under 35 U.S.C. 154(b) by 115 days.

(21) Appl. No.: 16/758,511

(22) PCT Filed: Aug. 23, 2018

(86) PCT No.: PCT/EP2018/000412
§ 371 (c)(1),
(2) Date: Apr. 23, 2020

(87) PCT Pub. No.: WO2019/081051
PCT Pub. Date: May 2, 2019

(65) Prior Publication Data
US 2020/0253622 A1     Aug. 13, 2020

(30) Foreign Application Priority Data
Oct. 27, 2017    (DE) ..................... 10 2017 010 033.0

(51) Int. Cl.
*A61B 17/16* (2006.01)
*A61B 17/17* (2006.01)

(52) U.S. Cl.
CPC .......... *A61B 17/1631* (2013.01); *A61B 17/17* (2013.01)

(58) Field of Classification Search
CPC . A61B 17/16; A61B 17/1613; A61B 17/1622; A61B 17/1624; A61B 17/1626; A61B 17/1628; A61B 17/1631; A61B 17/1662; A61B 17/1671
See application file for complete search history.

(56) References Cited

U.S. PATENT DOCUMENTS

| | | | |
|---|---|---|---|
| 5,938,616 A | 8/1999 | Eaton et al. | |
| 6,312,438 B1 * | 11/2001 | Adams | A61B 17/32002 606/159 |
| 8,568,417 B2 * | 10/2013 | Petrzelka | A61B 17/1631 606/80 |

(Continued)

FOREIGN PATENT DOCUMENTS

| | | |
|---|---|---|
| DE | 10036108 A1 | 11/2001 |
| DE | 10156917 A1 | 6/2003 |

(Continued)

*Primary Examiner* — Eric S Gibson
(74) *Attorney, Agent, or Firm* — McGlew and Tuttle, P.C.

(57) ABSTRACT

A medical device includes a guide unit having a guide tube with a longitudinal axis, a proximal first coupling part fixedly connected to the guide tube, and a distal pivoting head with a cylindrical surface. An actuating tube is axially movable in the guide tube and is connected to the pivoting head. The actuating tube causes a pivoting movement of the pivoting head via a proximal operating element. In the device, in order to orient a distal guide element for a rotatable surgical tool more precisely and thus angularly orient the working head of such a tool, the operating element is pivotable about the longitudinal axis and causes the pivoting movement of the pivoting head by the axial displacement of the actuating tube.

16 Claims, 5 Drawing Sheets

(56) References Cited

U.S. PATENT DOCUMENTS

| | | | |
|---|---|---|---|
| 9,101,369 B2 | 8/2015 | Ries | |
| 9,119,639 B2 * | 9/2015 | Kuntz | A61B 17/1631 |
| 9,439,634 B2 * | 9/2016 | Ries | A61B 17/1637 |
| 9,610,083 B2 * | 4/2017 | Kuntz | A61B 17/1631 |
| 9,839,443 B2 * | 12/2017 | Brockman | A61B 17/3478 |
| 10,178,998 B2 * | 1/2019 | Guo | A61B 17/1633 |
| 10,874,290 B2 * | 12/2020 | Walen | A61B 17/1659 |
| 2009/0023988 A1 * | 1/2009 | Korner | A61B 17/1624 600/106 |
| 2010/0217269 A1 * | 8/2010 | Landes | A61B 17/1617 606/84 |
| 2011/0152867 A1 * | 6/2011 | Petrzelka | A61B 17/8875 606/80 |
| 2011/0166575 A1 * | 7/2011 | Assell | A61B 17/1671 606/79 |
| 2013/0041377 A1 * | 2/2013 | Kuntz | A61B 17/1642 606/80 |
| 2013/0165908 A1 | 6/2013 | Purdy et al. | |
| 2015/0231365 A1 | 8/2015 | Stenzel et al. | |
| 2015/0366566 A1 * | 12/2015 | Kuntz | A61B 17/1631 606/80 |
| 2016/0015251 A1 * | 1/2016 | Suehara | A61B 1/0057 604/95.04 |
| 2016/0106442 A1 * | 4/2016 | Guo | A61B 17/1631 606/80 |
| 2018/0193036 A1 * | 7/2018 | Purdy | A61B 17/1613 |
| 2018/0242962 A1 * | 8/2018 | Walen | A61B 17/1659 |
| 2020/0008814 A1 * | 1/2020 | Muser | A61B 17/1617 |
| 2020/0253622 A1 * | 8/2020 | Ries | A61B 1/00128 |

FOREIGN PATENT DOCUMENTS

| | | |
|---|---|---|
| DE | 69837488 T2 | 12/2007 |
| DE | 102010024136 A1 | 12/2011 |
| DE | 102012008970 B3 | 6/2013 |
| DE | 102015204946 A1 | 9/2016 |
| EP | 2393435 B1 | 12/2012 |
| EP | 2790596 A1 | 10/2014 |
| EP | 2790596 B1 | 6/2015 |
| WO | 9915090 A1 | 4/1999 |

\* cited by examiner

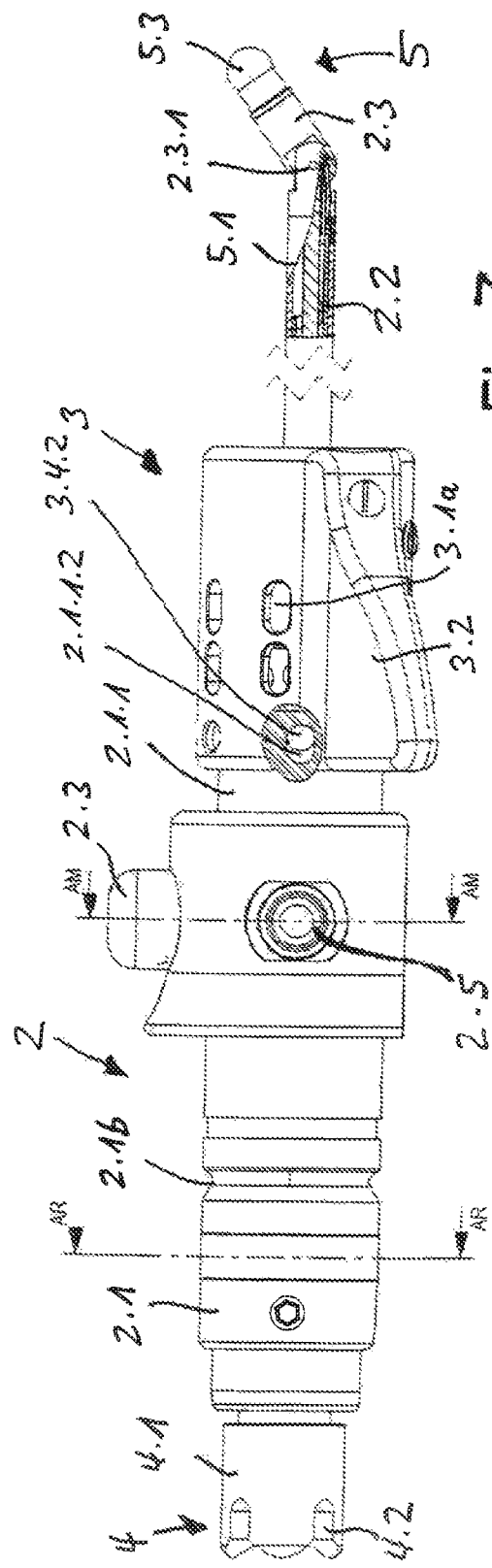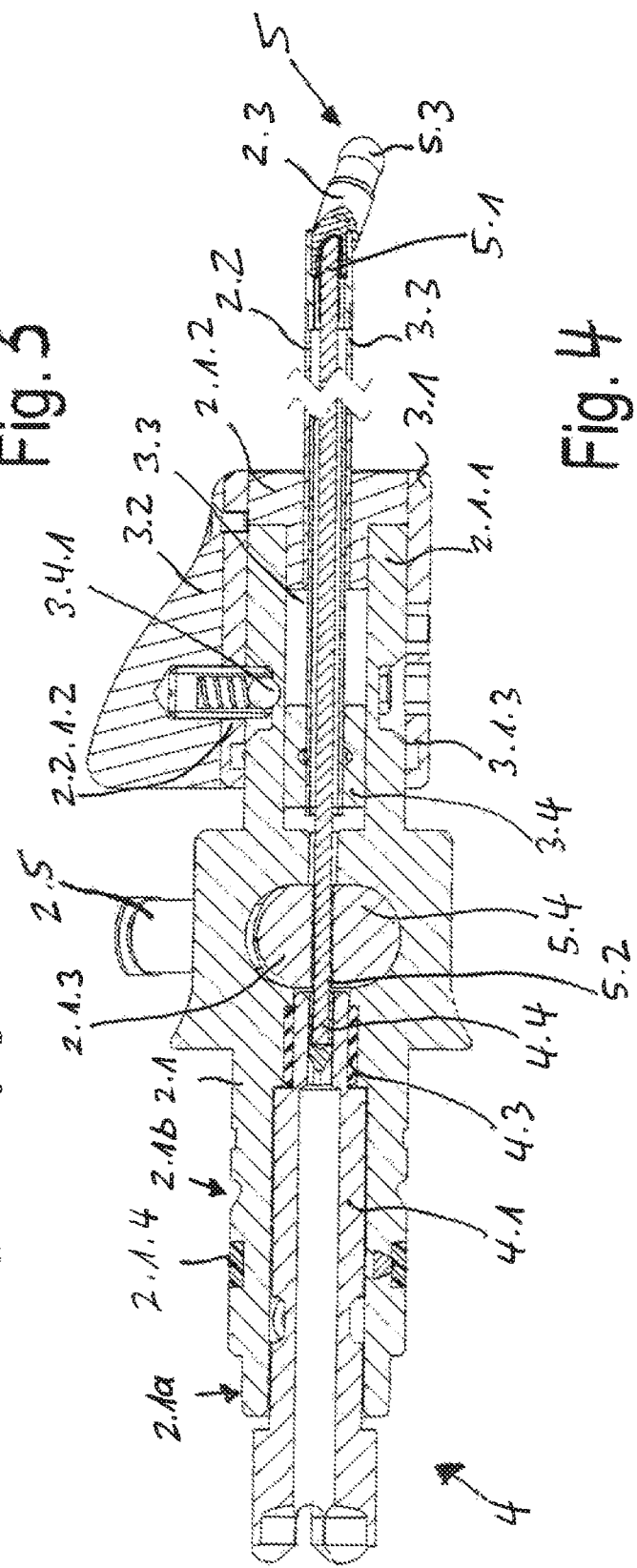

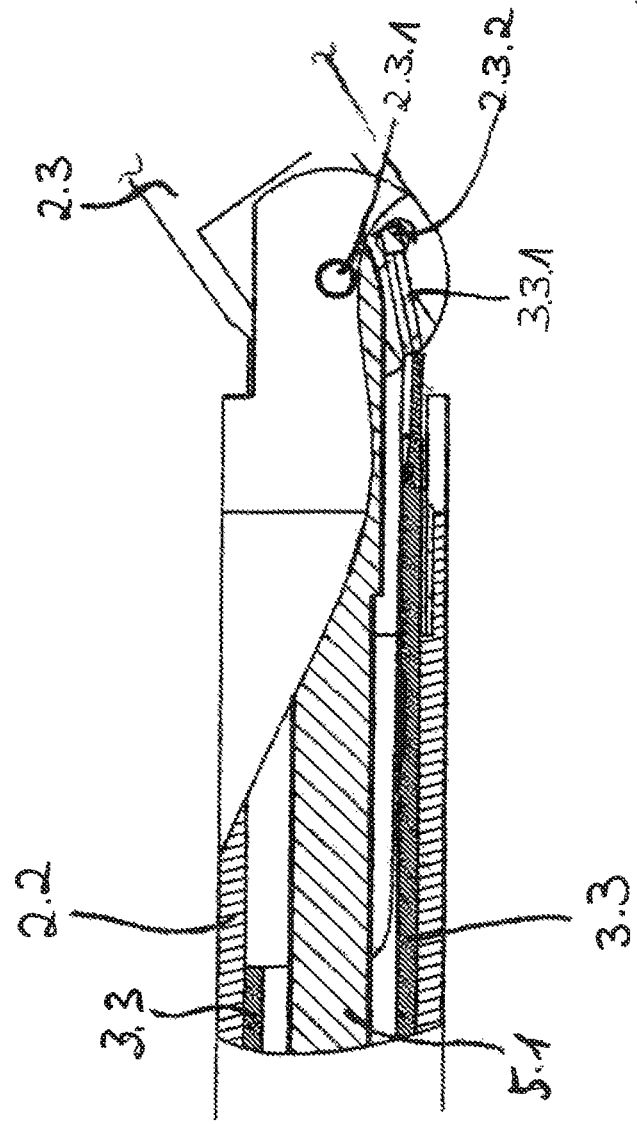

MEDICAL DEVICE

CROSS REFERENCE TO RELATED APPLICATIONS

This application is a United States National Phase Application of International Application, PCT/EP2018/000412 filed Aug. 23, 2018, and claims the benefit of priority under 35 U.S.C. § 119 of German Application 10 2017 010 033.0, filed Oct. 27, 2017, the entire contents of which are incorporated herein by reference.

TECHNICAL FIELD

The invention relates to a medical device comprising a guide unit having a guide tube with a longitudinal axis, a proximal first coupling part being fixedly connected to the guide tube, and a distal pivoting head with a cylindrical surface, said medical device also comprising an actuating tube which is axially movable in the guide tube and is connected to the pivoting head, said actuating tube being axially displaceable by an operating element by a pivoting movement of the pivoting head.

TECHNICAL BACKGROUND

A generic medical device is generally known from EP 2 790 596 B1. In this device, a guide section bent laterally relative to the longitudinal axis of the device is provided at the distal end for the non-axial orientation of the working head of a rotatable surgical tool, such as a milling cutter or a drill, in a guide part of the device.

Furthermore, DE 100 36 108 A1 discloses a surgical instrument which has at the distal end thereof a housing-like receptacle for the rotatable mounting of a jaw part, which is pivotably articulated on a distal end of a hollow shank. The actuation is carried out by a hand acting on a proximal lever, from the proximal end via an actuating rod by means of a gear mechanism which acts on the proximal end thereof. The operating mechanism is extremely complex, has considerable lateral or radial space requirements, and requires operation with the entire hand, including movement thereof relative to the arm of an operator.

SUMMARY

The invention is therefore based on the object of developing a generic device in such a way that, with a simple design, it results in a small space requirement for the configuration of the pivoting mechanism itself, while leaving a cavity for a surgical workpiece on the one hand, and on the other hand a simple and space-saving configuration of the proximal operating elements, an exact pivoting positioning of a distal pivoting element, and thus the orientation of a tool head determined by the latter.

According to the invention, the above object is achieved in a generic device in that the actuating tube can be displaced by pivoting the operating element.

A preferred embodiment provides that the axial movement of the guide tube is carried out via a link guide having a slot which extends in the circumferential direction at an angle not equal to 90° (≠90°) to the axis and a pin guided therein, wherein the pin is further fixedly connected to the guide tube and the slot is formed on a cylinder jacket which is fixed, in particular in one piece, to the operating element.

In addition, preferred developments provide that the pins each engage a radially oriented, elongated hole extending in the direction of the axis in a part which is fixedly connected to the guide tube, in particular a cylinder part, wherein in particular the pivoting head is pivotable relative to the guide tube via diagonally opposite joints formed at the distal end of the guide tube. In order to ensure the necessary space for the drive shaft of a tool to pass through, especially in the distal area, further developments provide that the actuating tube acts with a tab eccentrically in a proximal area of the pivoting head for the pivoting movement thereof, wherein latching depressions are arranged next to one another in the circumferential direction at an angle unequal to 90° to the axis in a cylinder jacket part connected to the guide tube and a spring pin connected to the operating element and engaging in the latter.

A precise positioning of the angular position can be achieved by means of a rotating unit which is rotatable relative to the guide unit.

In addition, the device according to the invention can be configured in a preferred embodiment for connection to the output shaft of a rotating drive in such a way that the rotating unit has a second coupling part which is arranged axially fixed but rotatable in the first coupling part, wherein preferably the rotating unit, in particular the second coupling part thereof, has coupling slots for a rotationally fixed connection to an output shaft of the pressure drive and the first coupling part has formations—preferably in the form of slots and an annular groove—for the axially and rotationally fixed connection to a drive and/or the housing of a drive.

Further developments provide a surgical rotating tool that is rotatable relative to the guide and actuating unit, but that can be axially fixed to the latter, wherein in particular the rotating tool has, at the proximal end of a shank, a non-cylindrical, preferably square, configuration for non-rotatable engagement in a corresponding non-cylindrical, preferably square, recess of the second coupling unit.

In addition, it can preferably be provided that a shank of the tool having a tapered area engages in the opening of a release and blocking element of the first coupling part.

Further preferred configurations are characterized in that the actuating tube is arranged coaxially in the guide tube and/or that the outer diameter of the actuating tube corresponds to the inner diameter of the guide tube.

The coupling elements can preferably be coupled as shown in EP 2 393 435 B1. The above-mentioned connection configurations of the coupling elements are designed in such a way that a connection described in that publication is possible with a drive. In this respect, the disclosure content of the cited publication is completely incorporated in the disclosure content of the application.

Further advantages and features of the invention result from the claims from the following description, in which an exemplary embodiment of the invention is explained in detail with reference to the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is the side view of the figure with a different distance into an outer part to show the formation of an underlying part;

FIG. 4 is a longitudinal section through the device according to the invention corresponding to A-B of FIG. 2;

FIG. 6 is an enlarged view of the pivoting head of FIG. 2.

DESCRIPTION OF PREFERRED EMBODIMENTS

Figure 1:
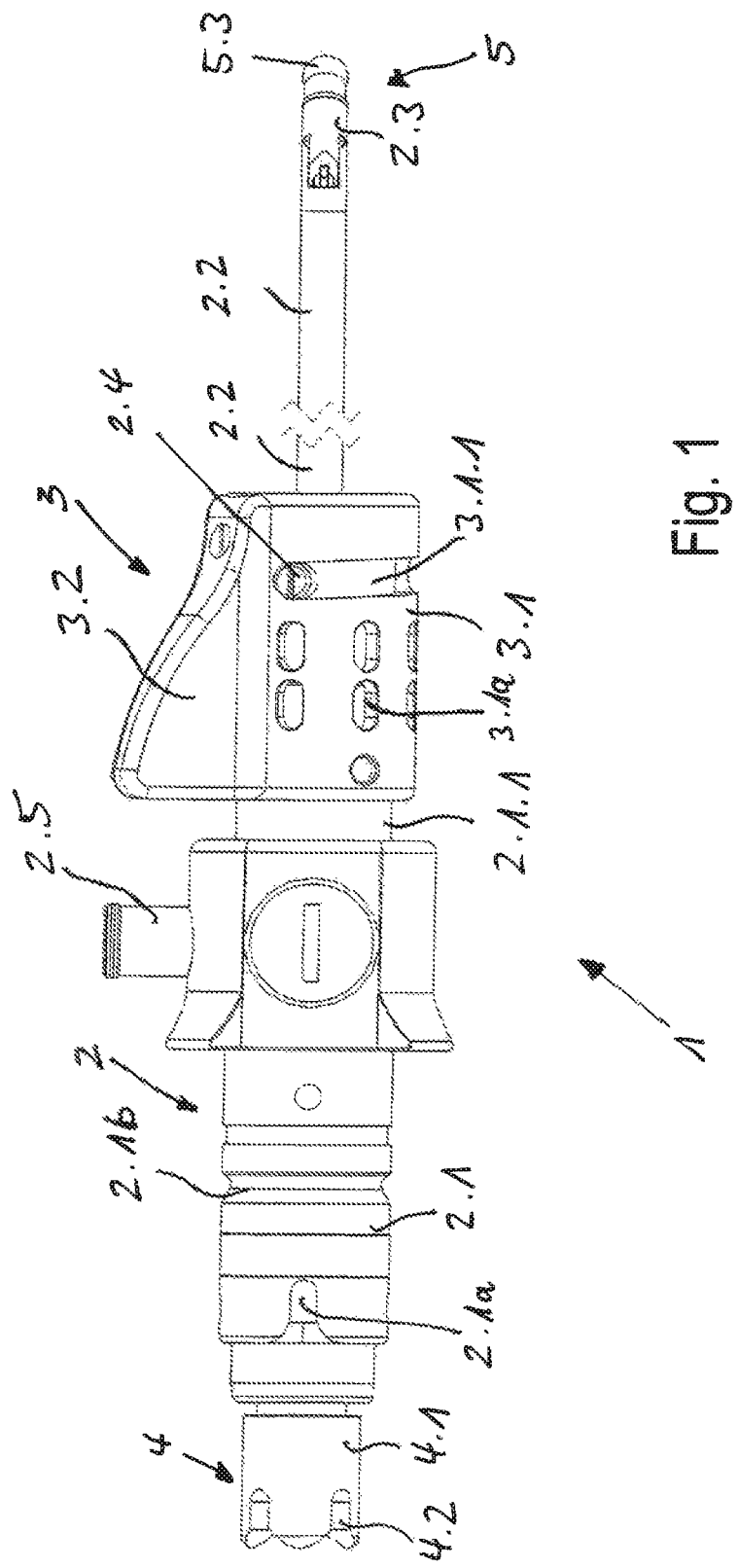
FIG. 1 is a side view of the medical device according to the invention.

Referring to the drawings, a device 1 according to the invention initially has a guide part 2. The guide part 2 is connected to a motor drive or the housing of a motor drive according to EP 2 393 435 B1 in a fixed manner, i.e. in a rotationally and axially fixed manner. The fixation takes place via the proximal longitudinal slots 2.1a and the annular groove 2.1b of a coupling part 2.1 of the guide part 2 in the manner described there.

A guide tube 2.2 of the guide part 2 is fixedly connected to the coupling part 2.1, that is to say in a rotationally and axially fixed and non-detachable manner. At the distal end of the guide tube 2.2, a pivoting head 2.3 with a cylindrical surface is pivotally arranged thereon. The articulated connection is formed by diametrically opposite joints 2.3.1 at the level of a central axis A of the guide tube 2.2 and the first coupling part 2.1.

In one piece with the first coupling part 2.1, a first cylinder jacket 2.1.1 is formed distally thereto (also FIG. 4), into which a pipe connection part 2.1.2 (FIG. 4) is inserted at the distal end, to which the guide tube 2.2 is connected and in a preferably materially fixed manner. The parts 2.1, 2.1.1, 2.1.2 and 2.2 mentioned are preferably made of stainless steel, wherein the materially fixed connections are each formed by means of laser welding on the one hand between the cylinder jacket 2.1.1 and the pipe connection part 2.1.2 in the form of a bush and on the other hand between the latter and the guide tube 2.2.

Approximately in the middle of the coupling part 2.1, a release and blocking element 2.1.3, preloaded by a spring (not shown), can be seen in the form of a push button, the function of which is described below.

Relative to the guide part 2, an actuating unit 3 is limitedly rotatably and axially movably provided.

For this purpose, the actuating unit 3 has a second cylinder jacket 3.1 which movably surrounds the first cylinder jacket 2.1.1 and has an actuating element 3.2 in the form of a tab which can be pivoted in the circumferential direction of the axis A, both of which are integrally formed with one another. The second cylinder jacket 3.1 is provided on one side of the actuating element 3.2 with a slot 3.1.1 which extends in the circumferential direction of the second cylinder jacket 3.1 and is oriented at an angle to the axis A≠90°, that is to say not perpendicular to the axis A. The extension angle of the slot 3.1.1 perpendicular to the axis A is only a few degrees, preferably 3° to 5°. A pin 2.4, for example in the form of a screwed-in headless slot screw, projects into the slot 3.1.1 and is fixedly connected to the first cylinder jacket 2.1.1. The slot 3.1.1 thus forms a link guide for the pin 2.4. A Luer lock 2.5 is provided on the side of the guide part 2 in order to enable rinsing.

Short axial slots 3.1a in the cylinder jacket 3.1 of the actuating unit allow better cleaning by rinsing and contribute to saving weight.

Figure 2:
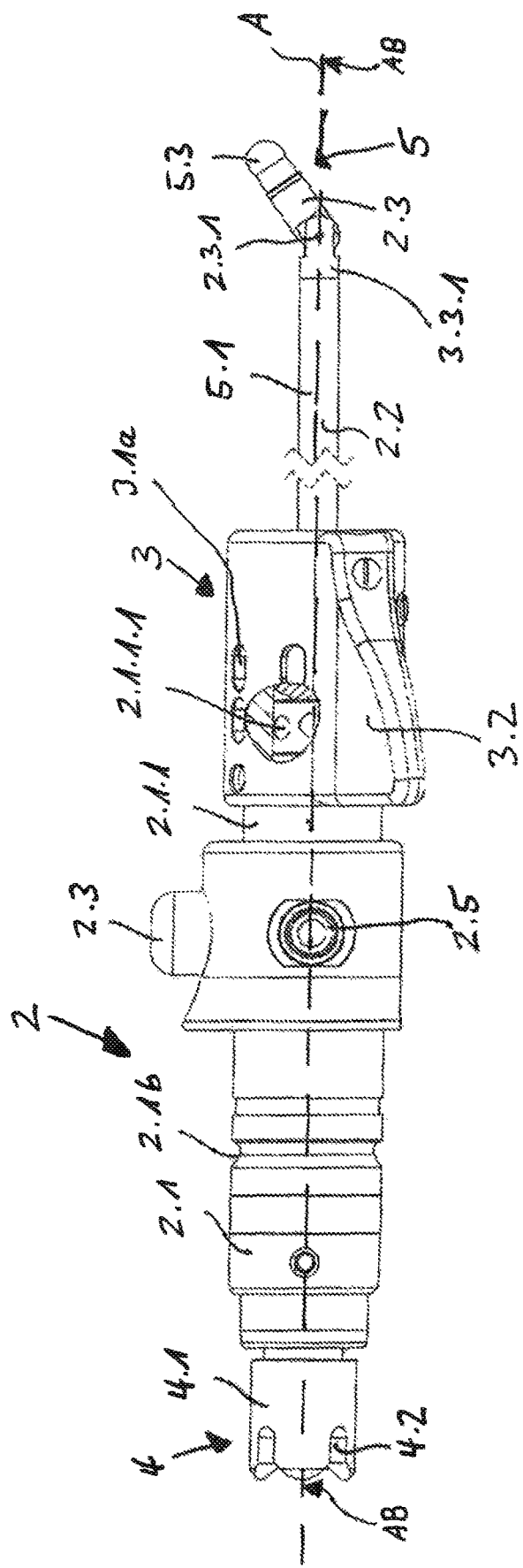
FIG. 2 is a side view at a different angular angle, partially cut.

As can be seen in FIG. 2, a plurality of depressions 2.1.1.1 are formed proximally to the arrangement of the pins 2.4 in the outer wall of the cylinder jacket 2.1.1 in the circumferential direction, likewise at the same angle as the slot 3.1.1 to the axis A, each in which—as can be seen in FIG. 4—a ball 3.1.2.2 of a spring pin 3.1.2 mounted in the cylinder jacket 3.1 and pre-loaded by a spring 3.1.2.1 can snap into the angular positions determined by the position of the depressions 2.1.1.1.

Figure 5:
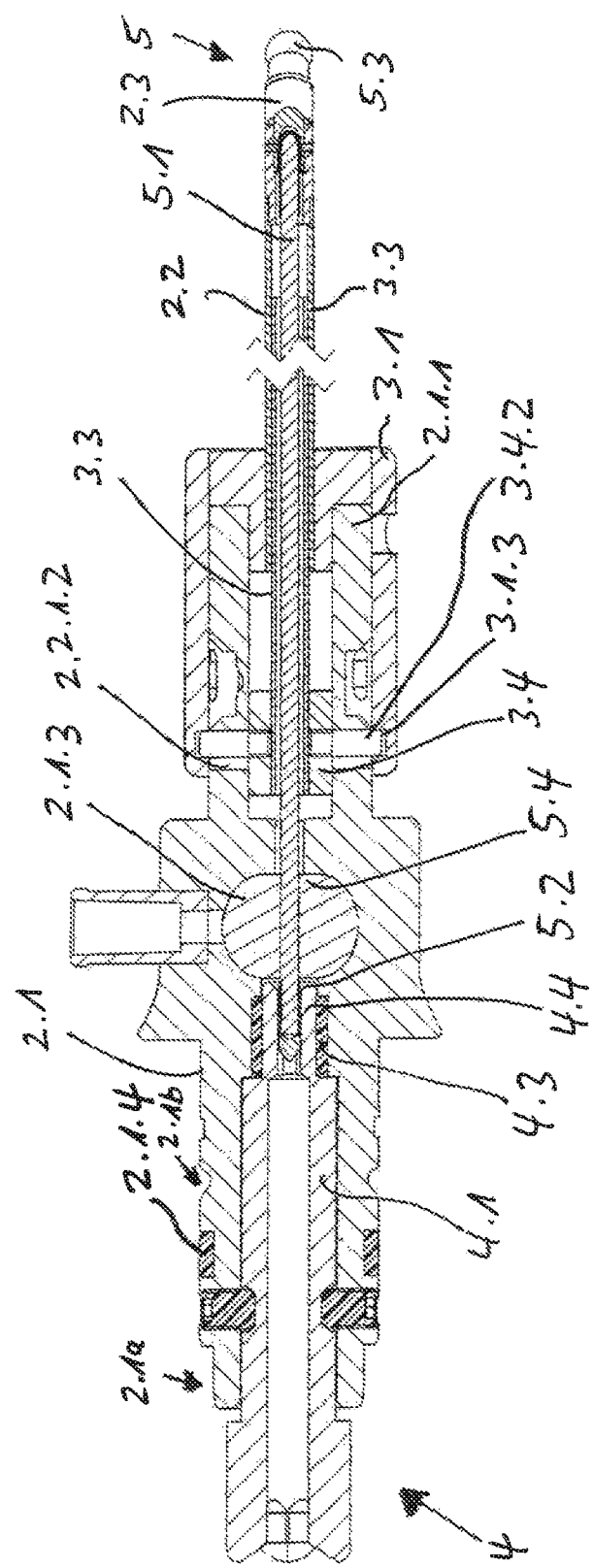
FIG. 5 is a longitudinal section at an angular angle of 90° to the section of FIG. 4.

As shown in FIGS. 3 and 5, an actuating tube 3.3 for the pivoting head 2.3 extends axially displaceably. The actuating tube 3.3 is fixed proximally, that is to say in a rotationally and axially fixed manner, to a bush 3.4 (FIG. 4), preferably in a materially fixed manner, in particular by laser welding. The bush 3.4 has two diametrically opposed radial threaded bores 3.4.1 (FIG. 5), into which radial pins 3.4.2 are screwed in the form of headless screws. The pins 3.4.2 extend through radial openings 2.1.1.2, which are formed in this area in the first cylinder jacket 2.1.1 in the axial direction as elongated holes, so that the pins 3.4.2 and also the actuating tube 3.3 connected via the bush 3.4 are axially displaceable or are movable over a limited distance in these radial openings 2.1.1.2 (FIG. 5). Radially outer ends of the pins 3.4.2 protrude into a radially inwardly oriented recess 3.1.3 of the second cylinder jacket 3.1 of the actuating unit 3 which corresponds to the transverse dimensions of the pins.

As shown in FIG. 6, the actuating tube 3.3 continues at its distal end in a distal tab 3.3.1, which engages around pins 2.3.2 arranged on both sides eccentrically to the joints 2.3.1 on the pivoting head 2.3.

The longitudinal sections of FIGS. 4, 5 show magnets 2.1.4 on the outer circumference of the coupling part 2.1 to detect the device connected to the drive (not shown), so that this speed and direction of rotation are automatically adjusted.

The pivoting head 2.3 is actuated as follows on the basis of the configuration described:

If the second cylinder jacket 3.1 is pivoted by a user engaging the tab 3.2 and pivoting it about the first cylinder jacket 2.1.1 and thus relative to the coupling part 2.1, the second cylinder jacket 3.1 is simultaneously moved axially in the direction of the axis A due to the link guide formed by the slot 3.1.1 and the pin 2.4. This axial movement is transmitted to the pins 3.4.2 and via the latter and the bushes 3.4 to the actuating tube 3.3, which is also moved axially in this way. This axial movement is transmitted to the pivoting head 2.3 via the tab or the attachment 3.3.1 and the eccentrically arranged pins 2.3.2 and pivot said pivoting head about the pivoting axis thereof formed by the joints 2.3.1 from an extended position into an angled position relative to the axis A, as can be seen in particular in FIG. 2.

It is thereby achieved that a surgical rotating tool which extends through the guide tube 2.2 and actuating tube 3.3 can work with a distal working head in an angular position to the axis, in particular the angular position shown in FIG. 2.

In FIGS. 1 to 5, a rotation unit 4 is also shown on the left. Firstly, the latter has a second coupling part 4.1 which is rotatably mounted in the first coupling part 2.1 and has coupling elements at its proximal end in the form of slots which are coaxial with the axis A and can be coupled to the output axis of a rotary drive in such a way as is disclosed in EP 2 393 435 B1.

The second coupling part 4.1 is rotatable in the first coupling part 2.1, in particular via a mounting 4.3, but is axially fixed (FIGS. 3, 5). It has an axially extending recess 4.4, which is not circularly symmetrical in cross section, for example a square recess, into which the proximal end of a shank 5.1, such as a drill or milling cutter, can be inserted in a rotationally fixed manner from the distal end of the device, that is to say from the pivoting head 2.3. For this purpose, the rotating tool 5 has a shank 5.1 which is cylindrical over the major part of its longitudinal extent, but this is formed at the proximal end corresponding to the recess 4.4 as a polygon 5.2, in particular a square. A tool head 5.3, for example in the form of a milling or drilling head, is provided at the distal end of the tool 5.

The axial fixation of the tool 5 takes place via the already mentioned push button 2.1.3, which has an axial opening, by means of which when the push button 2.1.3 is pressed to insert and remove the tool 5, the shank 5.1 including the square 5.2 at its proximal end up to the depression 4.4 can be pushed through and, when the push button 2.1.3 is released, the shaft 5.1 is axially fixed over a tapered area 5.4 under the action of the springs (not shown).

While specific embodiments of the invention have been shown and described in detail to illustrate the application of the principles of the invention, it will be understood that the invention may be embodied otherwise without departing from such principles.

The invention claimed is:

1. A medical device comprising:
    a guide unit having a guide tube with a longitudinal axis;
    a proximal first coupling part fixedly connected to the guide tube;
    a distal pivoting head with a cylindrical surface;
    a proximal operating element;
    an actuating tube which is axially movable in the guide tube and is connected to the pivoting head, causing a pivoting movement of the pivoting head by means of the proximal operating element, wherein the operating element is pivotable about the longitudinal axis and causes the pivoting movement of the pivoting head with axial displacement of the actuating tube; and
    a link guide, wherein the proximal operating element causes axial movement of the guide tube via the link guide having a slot, which extends in a circumferential direction at an angle not equal to 90° to the axis, and a pin guided in the slot.

2. A medical device according to claim 1, wherein:
    the link guide comprises a cylinder jacket; and
    the pin is fixedly connected to the guide tube and the slot is formed on the cylinder jacket which is fixed to the operating element.

3. A medical device according to claim 1, further comprising radially extending pins connected to the guide tube, and each engaging into an inwardly oriented guide groove having a diameter corresponding to a width thereof in an axial direction of the operating element.

4. A medical device according to claim 3, wherein the radially extending pins each engage through a radially oriented elongated hole extending in a direction of the axis in a part which is fixedly connected to the guide tube.

5. A medical device according to claim 1, wherein the pivoting head is pivotable relative to the guide tube via diagonally opposite joints formed at a distal end of the guide tube.

6. A medical device according to claim 1, wherein the actuating tube acts eccentrically with a tab in a proximal area of the pivoting head for the pivoting movement thereof.

7. A medical device according to claim 1, wherein:
    a cylinder jacket part is connected to the guide tube;
    a spring pin is connected to the operating element;
    latching depressions are arranged next to one another in a circumferential direction at an angle unequal to 90° to the axis in the cylinder jacket part connected to the guide tube and the spring pin is connected to the operating element and engages the cylinder jacket part.

8. A medical device according to claim 1, further comprising a rotating unit which is rotatable relative to the guide unit.

9. A medical device according to claim 8, wherein the rotating unit has a second coupling part arranged axially fixed but rotatable in the first coupling part.

10. A medical device according to claim 8, wherein the rotating unit has coupling slots for a rotationally fixed connection to a drive shaft.

11. A medical device according to claim 1, wherein the first coupling part has formations for axially and rotationally fixed connection to a drive and/or a housing of a drive.

12. A medical device according to claim 1, further comprising a surgical rotating tool rotatable relative to the guide and actuating unit and axially fixable to an actuating unit.

13. A medical device according to claim 12, further comprising a rotating unit which is rotatable relative to the guide unit, wherein the rotating unit has a second coupling part, wherein the rotating tool has a shank with a proximal end having a non-cylindrical configuration for non-rotatable engagement in a corresponding non-cylindrical recess of the second coupling part.

14. A medical device according to claim 12, wherein a shank of the tool has a tapered area engaging in an opening of a release and blocking element of the first coupling part.

15. A medical device according to claim 1, wherein the actuating tube is arranged coaxially in the guide tube.

16. A medical device according to claim 1, wherein an outer diameter of the actuating tube corresponds to an inner diameter of the guide tube.

* * * * *